US008815929B2

(12) United States Patent
Shanler et al.

(10) Patent No.: US 8,815,929 B2
(45) Date of Patent: *Aug. 26, 2014

(54) METHOD AND THERAPEUTIC/COSMETIC TOPICAL COMPOSITIONS FOR THE TREATMENT OF ROSACEA AND SKIN ERYTHEMA USING $\alpha_1$-ADRENOCEPTOR AGONISTS

(75) Inventors: Stuart D. Shanler, Pomona, NY (US); Andrew Ondo, Las Cruces, NM (US)

(73) Assignee: Allergan, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/901,755

(22) Filed: Oct. 11, 2010

(65) Prior Publication Data
US 2011/0034423 A1 Feb. 10, 2011

Related U.S. Application Data

(63) Continuation of application No. 10/763,807, filed on Jan. 22, 2004, now Pat. No. 7,812,049.

(51) Int. Cl.
A01N 43/50 (2006.01)
A61K 31/415 (2006.01)
C07D 233/00 (2006.01)

(52) U.S. Cl.
USPC ........................................ 514/401; 548/347.1

(58) Field of Classification Search
USPC ........................................ 514/401; 548/347.1
See application file for complete search history.

(56) References Cited

U.S. PATENT DOCUMENTS

| | | | |
|---|---|---|---|
| 4,853,216 A | 8/1989 | Koslo et al. | |
| 5,164,406 A * | 11/1992 | Helman et al. | 514/357 |
| 5,620,416 A * | 4/1997 | Riviere | 604/500 |
| 5,801,199 A * | 9/1998 | Greve et al. | 514/563 |
| 6,335,023 B1 | 1/2002 | Yu et al. | |
| 6,680,062 B2 | 1/2004 | Muizzuddin et al. | |
| 6,824,786 B2 | 11/2004 | Yu et al. | |
| 7,141,597 B2 | 11/2006 | Chow et al. | |
| 7,439,241 B2 | 10/2008 | DeJovin et al. | |
| 7,812,049 B2 | 10/2010 | Shanler et al. | |
| 7,838,563 B2 | 11/2010 | DeJovin et al. | |
| 7,977,335 B2 | 7/2011 | Gil et al. | |
| 8,053,427 B1 | 11/2011 | Buge et al. | |
| 2002/0034554 A1 | 3/2002 | Hsu et al. | |
| 2004/0020259 A1 | 2/2004 | Ohno | |
| 2004/0220259 A1 | 11/2004 | Yu et al. | |
| 2004/0242588 A1 | 12/2004 | Dejovin et al. | |
| 2004/0266776 A1 | 12/2004 | Gil et al. | |
| 2005/0020600 A1 | 1/2005 | Scherer | |
| 2005/0059664 A1 | 3/2005 | Gil et al. | |
| 2005/0222101 A1 | 10/2005 | Hutterer | |
| 2005/0256204 A1 | 11/2005 | Bitter, Sr. | |
| 2005/0271596 A1* | 12/2005 | Friedman et al. | 424/45 |
| 2005/0276830 A1 | 12/2005 | DeJovin et al. | |
| 2005/0281772 A1 | 12/2005 | Bromley et al. | |
| 2006/0171974 A1 | 8/2006 | DeJovin et al. | |
| 2006/0264515 A1 | 11/2006 | Dejovin et al. | |
| 2006/0293359 A1 | 12/2006 | Kusari et al. | |
| 2007/0048234 A1 | 3/2007 | Waugh et al. | |
| 2007/0082070 A1 | 4/2007 | Stookey et al. | |
| 2007/0225217 A1 | 9/2007 | Chappell et al. | |
| 2007/0225631 A1 | 9/2007 | Bowlin et al. | |
| 2008/0207627 A1 | 8/2008 | Gil et al. | |
| 2009/0060852 A1 | 3/2009 | DeJovin et al. | |
| 2009/0061020 A1 | 3/2009 | Theobald et al. | |
| 2009/0130027 A1 | 5/2009 | Shanler et al. | |
| 2010/0021402 A1 | 1/2010 | DeJovin et al. | |
| 2010/0130502 A1 | 5/2010 | DeJovin et al. | |
| 2011/0027201 A1 | 2/2011 | Shanler et al. | |
| 2011/0034423 A1 | 2/2011 | Shanler et al. | |
| 2011/0224216 A1 | 9/2011 | Andres et al. | |
| 2011/0286945 A1 | 11/2011 | DeJovin et al. | |
| 2011/0288096 A1 | 11/2011 | Graeber et al. | |
| 2012/0035123 A1 | 2/2012 | Jomard et al. | |
| 2012/0101141 A1 | 4/2012 | Buge et al. | |
| 2012/0149748 A1 | 6/2012 | Shanler et al. | |

FOREIGN PATENT DOCUMENTS

| | | |
|---|---|---|
| WO | 9926942 A1 | 6/1999 |
| WO | 0236144 A1 | 5/2002 |
| WO | 2004030743 A2 | 4/2004 |
| WO | 2005060948 A1 | 7/2005 |

OTHER PUBLICATIONS

Tan et al. "Randomized Placeo-controlled Trial of Metronidaole 1% Cream with Sunscreem SPF 15 in Treatment of Rosacea" Journal of Cutaneous Medicine and Surgery, 2002, pp. 529-534.*
Cunliffe et al. "Clonidine and Facial Flushing in Rosacea", 1977, British Med. J., p. 105.*
Fisher,D.A. "Adverse Effects of Topical Corticosteroid Use" West J Med, 1995, vol. 162, pp. 123-126.*
Acne.Org, www.acne.org/messageboard/index.php?showtopic=34267; Feb. 10, 2011.
Acneteam.Com, www.acneteam.com/home-remedies-to-heal-acne-quick.html ; Jul. 17, 2007.
Ahlquist, A Study of the Adrenotropic Receptors, *Am J Physiol.* (Jun. 1948), 153(3):586-600.
Bamford, et al., Rosacea: Current Thoughts on Origin, *Semin Cutan Med Surg.* (Sep. 2001), 20(3):199-206.
Bishop, Recent Advances in the Discovery of $\alpha 1$-Adrenoceptor Agonists, *Curr Top Med Chem.* (2007), 7(2):135-145.

(Continued)

Primary Examiner — Kendra D Carter
(74) Attorney, Agent, or Firm — Pepper Hamilton LLP

(57) ABSTRACT

The present invention is directed to the treatment of skin erythema as exhibited in rosacea and other conditions characterized by increased erythema (redness) of the skin. These conditions exhibit dilation of blood vessels due to a cutaneous vascular hyper-reactivity. In particular, the present invention is directed to a novel composition and method for the treatment of skin erythema using $\alpha_1$-adrenergic receptor ($\alpha_1$-adrenoceptor) agonists incorporated into cosmetic, pharmacological or dermatological compositions for topical application to the skin.

13 Claims, No Drawings

(56) References Cited

OTHER PUBLICATIONS

Calzada, et al., Alpha-Adrenoceptor Subtypes, *Pharmacol. Res.* (Sep. 2001), 44(3):195-208.
Chalothorn, et al., Differences in the Cellular Localization and Agonist-Mediated Internatilization Properties of the $\alpha_1$-Adrenoceptor Subtypes, *Mol Pharmacol.* (May 2002), 61(5):1008-1016.
Collagenex Corporation/IMS Demand Study as presented at the 4th Annual Healthcare Conference, New York, NY (Nov. 27-28, 2007).
Crassous, et al., Interest of $\alpha_2$-Adrenergic Agonists and Antagonists in Clinical Practice: Background, Facts and Perspectives, *Curr Top Med Chem.* (2007), 7(2):187-194.
Crawford, et al., Rosacea: I. Etiology, Pathogenesis, and Subtype Classification, *J Am Acad Dermatol.* (Sep. 2004), 51(3):327-341.
Cross, et al., Transdermal Penetration of Vasoconstrictors—Present Understanding and Assessment of the Human Epidermal Flux and Retention of Free Bases and Ion-Pairs, *Pharm Res.* (Feb. 2003), 20(2):270-274.
Cunliffe, et al., Clonidine and Facial Flushing in Rosacea, *Br Med J.* (Jan. 8, 1977), 1(6053):105.
Fisher, Adverse Effects of Topical Corticosteroid use, *West J Med.* (Feb. 1995), 162(2):123-126.
Gentili, et al., Agonists and Antagonists Targeting the Different $\alpha_2$-Adrenoceptor Subtypes, *Curr Top Med Chem.* (2007), 7(2):163-186.
Guimarães, et al., Vascular Adrenoceptors: An Update, *Pharmacol Rev.* (Jun. 2001), 53(2):319-356.
Health Boards, www.healthboards.com/boards/showthread.php?t=5725&highlight=visine+zits; Jul. 17, 2007.
Hieble, Subclassification and Nomenclature of $\alpha$-and $\beta$-Adrenoceptors, *Curr Top Med Chem.* (2007), 7(2):129-134.
Jarajapu, et al., Functional Characterization of $\alpha_1$-Adrenoceptor Subtypes in Human Subcutaneous Resistance Arteries, *J Pharmacol Exp Ther* (Nov. 2001), 299(2):729-734.
Jenni, Information Connection: Tips on Treating Acne, www.mindconnection.com/library/health/acnecare.htm; Jul. 17, 2007.
Kirstein, et al., Autonomic Nervous System Pharmacogenomics: A Progress Report, *Pharmacol Rev.* (Mar. 2004), 56(1):31-52.
Leech, et al., Different $\alpha$-adrenoceptor subtypes mediate constriction of arterioles and venules, *Am. J. Phys.* (Feb. 1996), 39(2):H710-H722.
Parodi, et al., Flushing in Rosacea: An Experimental Approach, *Arch Dermatol Res.* (1980), 269(3):269-273.
Pelle, et al., Rosacea: II. Therapy, *J Am Acad Dermatol.* (Oct. 2004), 51(4):499-512.
Peter Lama'S Beauty Solutions, Tips for Beautiful Face and Body Skin, Beauty Magazine, www.lamasbeauty.com/beauty/solutions/tips_face_skin.htm; Jul. 17, 2007.
Piascik, et al., $\alpha_1$-Adrenergic Receptors: New Insights and Directions, *J Pharmacol Exp Ther.* (Aug. 2001), 298(2):403-410.
Pigini, et al., Structure-Activity Relationship at $\alpha$-Adrenergic Receptors Within a Series of Imidazoline Analogues of Cirazoline, *Bioorg Med Chem.* (May 2000), 8(5):883-888.
Plewig, et al., Acne and Rosacea, 2nd Rev. Ed., Springer-Verlag, Berlin/New York (Feb. 27, 2002), pp. 433-475.
Powell, Clinical Practice: Rosacea, *N Engl J Med.* (Feb. 24, 2005), 352(8):793-803.
Rona'S Skin Remedies, Beauty and Style, www.beauty.ivillage.com/skinbody/facecare/0,,8h9s,00.html; Jul. 17, 2007.
Sams, Untoward Response with Topical Fluorouracil, *Arch Dermatol.* (Jan. 1968), 97(1):14-22.
Scruggs, et al., The teardrop sign: a rare dermatological reaction to brimonidine, *Br. J. Ophthalmol.* (Jun. 2000), 84(6):667.
Shanler, et al., Successful Treatment of the Erythema of Flushing of Rosacea Using a Topically Applied Selective $\alpha_1$ Adrenergic Receptor Agonist, Oxymetazoline, *Arch Dermatol.* (Nov. 2007), 143(11):1369-1371.
Speake, et al., 2-(Anilinomethyl)imidazolines as $\alpha_1$ Adrenergic Receptor Agonists: $\alpha_{1a}$ Subtype Selective 2' Heteroaryl Compounds, *Bioorg Med Chem Lett.* (Mar. 24, 2003), 13(6):1183-1186.
Tetrahydrozoline hydrochloride, www.sigmaaldrich.com/catalog/search/ProductDetail/SIGMA/T4264; Jul. 17, 2007.
Van Zuuren, et al., Systematic Review of Rosacea Treatments, *J Am Acad Dermatol.* (Jan. 2007), 56(1):107-115.
Wilkin, et al., Standard classification of rosacea: Report of the National Rosacea Society Expert Committee on the Classification and Staging of Rosacea, *J Am Acad Dermatol.* (Apr. 2002), 46(4):584-587.
Wilkin, Oral Thermal-Induced Flushing in Erythematotelangiectatic Rosacea, *J Invest Dermatol.* (Jan. 1981), 76(1):15-18.
Wilkin, Why is flushing limited to a mostly facial cutaneous distribution?, *J. Am. Acad. Dermatol.* (Aug. 1, 1988), 19(2 Pt 1):309-313.
Dahl et al., "Topical Metronidazole Maintains Remissions of Rosacea", *Arch Dermatol*, (1998), 34(6):679-683.
Kim, et al., Rosacea (erythematotelangiectatic type) effectively improved by topical xylometazoline, The Journal of Dermatology, 2010, pp. 1-3, vol. 37, Japenese Dermatological Association, Korea.
Wymenga et al., Management of Hot Flushes in Beast Cancer Patients, Acta Oncologica, 2002, pp. 269-275, vol. 41, No. 3.
Nielson, et al., Postjunctional Alpha 2-adrenergic receptors mediate vasoconstriction in human subcutaneous resistance vessels, British Journal of Pharmacology, 1989, pp. 829-834, vol. 97, No. 3.
Wilkin, Jonathan K., Effect of Subdepressor Clonidine on Flushing Reactions in Rosacea, Archives of Dermatology, Mar. 1983, pp. 211-214, vol. 119.
Burke, et al., Preclinical Evaluation of Brimonidine, Survey of Ophthalmol, Nov. 1996, vol. 41 Suppl 1, Department of Biological Sciences, pp. 9-18, Irvine, California.
Rebora, The Management of Rosacea, American Journal of Clinical Dermatology, 2002, pp. 489-496, vol. 3, Department of Endocrinological and Metabolic Diseases, Section of Dermatology, University of Genoa, Genoa, Italy.
Guarrera, et al., Flushing in Rosacea: A Possible Mechanism, Archives Dermatol Res, 1982, pp. 311-316, vol. 272.
Chotani, et al., Silect Alpha(2C)-adrenergic Receptors Enable Cold-induced Vasoconstriction in Cutaneous Arteries, American Journal of Physiol Hear Circ Physiol, Apr. 2002, pp. 1075-1083, vol. 278, Heart and Lung Institute, Ohio State University, Columbus Ohio, USA.
Declaration of Dr. Andrew Ondo, Jul. 17, 2007.
Du Vivier et al., Tachyphylaxis to the Action of Topically Applied Corticosteroids, Arch Dermatol/vol. 111, May 1975, pp. 581-583.
Jansen et al., Rosacea: classification and treatment, Journal of the Royal Society of Medicine, Vol. 90, Mar. 1997, pp. 144-150.
Odom et al., Standard Management Options for Rosacea, Part 2: Options According to Subtype, Cutis, vol. 87, Aug. 2009, pp. 97-104.
Bratslavsky, DERMAdoctor, Skincare articles: your prescription for beautiful skin, www.dermadoctor.com/pages/newsletter221.asp. printed from the Internet Jul. 17, 2007.
Leal, Miscellaneous e-mail communication; Nov. 6, 2001.
Gupta et al., Rosacea and its Management: an overview, *JEADV*, (2005), 19:273-285.

\* cited by examiner

METHOD AND THERAPEUTIC/COSMETIC TOPICAL COMPOSITIONS FOR THE TREATMENT OF ROSACEA AND SKIN ERYTHEMA USING $\alpha_1$-ADRENOCEPTOR AGONISTS This application is a continuation of U.S. patent application Ser. No. 10/763,807 filed Jan. 22, 2004, now U.S. Pat. No. 7,812,049 issued Oct. 12, 2010, the disclosure of which is incorporated by reference in its entirety.

FIELD OF THE INVENTION

The present invention is directed to the field of Rosacea and particularly to treatments for Rosacea.

BACKGROUND OF THE INVENTION

Rosacea is a chronic inflammatory disease associated with dilation of the facial blood vessels in humans. Rosacea affects the skin of the central face, especially the nose, cheeks, chin and forehead. The disease may progress with age. Rosacea may begin in individuals less than 20 years of age but peaks between the ages of 40 and 50.

Early rosacea is characterized by recurrent episodes of flushing or blushing that often develop into persistent or permanent redness of the skin. Flushing may be triggered by numerous non-specific stimuli including sun exposure, heat, cold, alcoholic drinks, spicy foods, chemical irritation and strong emotions. With time, papules, pustules, blood vessel formation and hypertrophy of sebaceous glands may develop. Symptoms of facial discomfort can include tightness, itching, burning, warmth, stinging and/or tingling.

Classically, treatment includes anti-infectious agents, such as, metronidazole, clindamycin, precipitated sulfur, sodium sulfacetamide, benzoyl peroxide, azelaic acid, or tetracycline-class antibiotics. But these agents do not affect the vascular component of this condition or the resulting skin redness. Other treatment strategies include avoidance of triggering factors, irritating stimuli, and limiting sun exposure.

Lasers are now available to treat some of the telangiectasias and redness in rosacea. An excellent review of the currently available lasers is found in the article: Getting the Red Out, presented in the $6^{th}$ Annual Acne and Rosacea issue of Skin & Aging, August 2003, pages 74-80. However, as is clearly stated in that review by Michael Krivda, "not all facial vessels respond to currently available laser therapies."

Furthermore, although some telangiectasias are treatable with laser, treatment of these blood vessels with medications has been completely ineffective. James Q. Del Rosso, D O, clinical assistant professor, Department of Dermatology, University of Nevada School of Medicine, Las Vegas, stated in: Medical Management of Rosacea with Topical Agents: A thorough appraisal of available treatment options and recent advances, Cosmetic Dermatology, August 2003: "Currently available medical therapies for rosacea have not been shown to reduce the number of facial telangiectasias."

Finally, there is currently no consistently effective treatment of any kind for the acute flushing and blushing of rosacea. John E. Wolf, Jr, MD, professor and chairman of the Department of Dermatology, Baylor College of Medicine, Houston, Tex., addressed this very issue in the meeting highlights for the Fall Clinical Dermatology Conference in Las Vegas, Nev., 2002. According to Dr. Wolf, "By far the most difficult-to-treat and challenging patients with rosacea are the patients who flush and blush. Indeed, no therapy works consistently in these patients." Dr. Wolf further asserted, "In my opinion, lasers are the most effective treatment for erythemato-telangiectatic rosacea, but I think they are much less effective for flushing and blushing patients. Some patients will respond but most do not."

Similarly, no consistently effective treatment has existed for the redness that may develop in other forms of discreet skin erythemas particularly those due to vascular cutaneous hyper-reactivity, including the redness associated with acute sunburn, chronic solar damage, inflammatory acne, or emotionally or physiologically induced erythema. These conditions may also be accompanied by itching, burning, or pain with resulting significant irritation for individuals suffering therefrom.

Thus, there exists a need for effective treatment of skin redness and of the state of vascular cutaneous hyper-reactivity as exhibited in rosacea or discreet erythemas.

Although the cause of rosacea is still unknown, it is clear that individuals with this condition exhibit a cutaneous hyper-reactivity with dilation of blood vessels of the skin. An acute dilation of blood vessels leads to periodic episodes of flushing or blushing. The more chronic form, felt to be due to blood vessels dilating over decades and eventually remaining dilated permanently, manifests as permanent redness of the skin or fine visible blood vessel formation (telangiectasias) within the skin.

A plethora of topical dermatological, cosmetic and pharmaceutical preparations and numerous methods and apparati exist for the treatment of rosacea, however, none has been proven consistently effective in treating and/or preventing the vascular dilatation which characterizes the erythema and flushing which are hallmarks of the disease.

A number of patents have been issued related to rosacea treatments. U.S. Pat. No. 4,837,378 to Borgman, describes a topical aqueous gel containing metronidazole and polyacrylic acid for the treatment of rosacea. U.S. Pat. No. 6,174,534 to Richard et al. claims the use of a cosmetic composition containing from 1-5% of a C.sub.12-C.sub.24 fatty acid, from 5 to 15% of an ester of C.sub.12-C.sub.24 fatty acid and of a C.sub.2-C.sub.3 polyalkylene oxide fragment containing from 2 to 100 polyalkylene oxide residues, from 1 to 20% of an optionally polyoxyalkylenated C.sub.12-C.sub.22 fatty acid glyceride containing from 0 to 20 ethylene oxide residues, from 1 to 20% of an ester of a C.sub.12-C.sub.24 fatty acid and of a C.sub.1-C.sub.6 alcohol, from 0.1 to 10% of glycerol, from 0.1 to 3% of a C.sub.12-C.sub.24 fatty alcohol and water, where the composition is free of metronidazole, lanthanide, tin, zinc, manganese, yttrium, cobalt, barium strontium salt, and non-photosynthetic filamentous bacteria.

U.S. Pat. No. 5,972,993 describes a method of treating rosacea with a topically applied compound comprising an antioxidant ("free-radical scavenger") mixed in an inert vehicle.

U.S. Pat. No. 5,569,651, to Garrison, et al discusses the use of a combination of salicylic acid and lactic acid to treat the sensitive skin of rosacea.

U.S. Pat. No. 5,438,073, to Saurat, et al claims the use of dermatological compositions containing retinoids for the treatment of rosacea.

U.S. Pat. No. 6,180,699 to Tamarkin, et al claims the use of dermatological preparations containing mono or diesters of alpha, omega dicarboxylic acids for the treatment of the hyperkeratinization and seborrheic components of rosacea.

U.S. Pat. No. 6,176,854 to Cone, claims the use of a Holmium laser system for the coagulation of some of the dilated blood vessels associated with rosacea to attempt to decrease the redness of the condition.

U.S. Pat. No. 6,306,130 describes the use of a methods and apparati for heating and inducing necrosis and degradation of blood vessels with an external energy source (e.g. a laser) to permanently weld blood vessels and treat various conditions such as varicose veins and telangiectasias.

Additionally, new insights and theories regarding the pathogenesis of rosacea have led to the development of treatment strategies focusing on the role of neurotransmitters and other potential mediators of vascular dilatation and hyperreactivity.

U.S. Pat. No. 5,958,432 to Breton, et al. describes the use of cosmetic/pharmaceutical compositions comprised of an effective Substance P antagonist of at least one beta-adrenergic agonist for the treatment of a variety of mammalian disorders mediated by an increase in the synthesis and/or release of Substance P including cutaneous disorders and sensitive skin and may generally relieve the irritation of rosacea (but has no direct vasoconstrictive properties).

U.S. Pat. No. 5,932,215 to de Lacharriere et al. is directed to the development of therapeutic/cosmetic compositions comprising CGRP (calcitonin gene related peptide) antagonists, Substance P antagonists, for treating skin redness, rosacea and discrete erythema afflicting a mammalian, notably human patient. Individuals are treated by administrating a therapeutically/cosmetically effective amount of at least one CGRP antagonist, advantageously in combinatory mixture with at least one antagonist of a neuropeptide other than CGRP, e.g., a substance P antagonist, and/or at least one inflammation mediator antagonist.

The notion of administering alpha-2 adrenoceptor agonists to alleviate the symptoms of diseases modulated by activity of these receptors has been investigated. U.S. Pat. No. 5,916,900 to Cupps, et al. relates to the use of certain substituted 7-(2-imidazolinylamino)quinolone compounds which have been found to be alpha-2 adrenoreceptor agonists and are useful for the treatment of disorders modulated by alpha-2 adrenoceptors. Such disorders include sinusitis, nasal congestion, numerous pulmonary and cardiovascular disorders, gastrointestinal disorders such as diarrhea, irritable bowel syndrome and peptic ulcer, conditions associated with chronic pain, migraine, and substance-abuse withdrawal syndrome. The subject invention involved novel compounds and compositions which have activity when administered perorally, parenterally, intranasaly and/or topically.

Finally, $\alpha_1$-adrenoceptor agonists have been historically used on ocular mucosal tissue to treat the conjunctival redness associated with allergic and other conditions, and to nasal mucosa as a decongestant for the treatment of allergic rhinitis and other conditions.

Also, U.S. Pat. No. 6,136,337 provides a composition for rectal mucosal administration suitable for curing hemorrhoids which includes an acrylic acid polymer, a vasoconstrictor, including tetrahydrozoline hydrochloride, naphazoline hydrochloride, phenylepherine hydrochloride or oxymetazoline hydrochloride and a rectal tissue-curing agent.

Critical to understanding the effects of catecholamines and related sympathomimetic agents is an understanding of the classification and properties of the different types of adrenergic receptors (adrenoceptors) that mediate their response. Although structurally related, different adrenoceptors regulate distinct physiological processes by controlling the synthesis or release of a variety of second messenger chemicals or compounds.

Additional general references of interest are set forth below.

Cross, E. Transdermal penetration of vasoconstrictors-present understanding and assessment of the human epidermal flux and retention of free bases and ion-pairs. *Pharm Res.* 2003 February; 20(2):270-4.

Daly, C J et al. Cellular Localization and Pharmacological Characterization of Functioning Alpha-1 Adrenoceptors by Fluorescent Ligand Binding and Image Analysis Reveals Identical Binding Properties of Clustered and Diffuse Populations of Receptors. *Pharmacology and Experimental Therapeutics.* 1998; 286(2):984-990.

Del Rosso, J Q. Medical Management of Rosacea With Topical Agents: A Thorough Appraisal of Available Treatment Options and Recent Advances. *Cosmetic Dermatology.* 2003; 16(8):47-55.

Hoffman B: Catecholamines, Sympathomimetic Drugs, and Adrenergic Receptor Antagonists, in *Goodman & Gilman's The Pharmacological Basis of Therapeutics, Tenth Edition*, edited by Hardman J and Limbird L. New York, N.Y., McGraw-Hill, 2001, pp. 215-249.

Hoffman B and Taylor P: Neurotransmission: The Autonomic and Somatic Motor Nervous Systems, in *Goodman & Gilman's The Pharmacological Basis of Therapeutics, Tenth Edition*, edited by Hardman J and Limbird L. New York, N.Y., McGraw-Hill, 2001, pp. 129-153.

Hudson, A L et al. In vitro and in vivo approaches to the characterization of the alpha2-adrenoceptor. *J Auton Pharmacol.* 1999 December; 19(6):11-20.

Krivda, M. Getting the Red Out. *Skin & Aging.* 6th Annual Acne & Rosacea Issue. 2003; 11(8):74-80.

Odom R B et al. *Andrews' Diseases of the Skin, Ninth Edition*, Philadelphia, W.B. Saunders, 2000, pp 301-303.

Plewig, G et al: Rosacea, in *Fitzpatrick's Dermatology in General Medicine, Fifth Edition*, edited by Irwin Freedberg et al. New York, N.Y., McGraw-Hill, 1999, pp 785-794.

Wolf J. 'Toughest Patients' May Be the Ones You See Each Day. in Meeting Highlights: 21st Anniversary Fall Clinical Dermatology Conference, Las Vegas, Nev., 2002: p. 1-4.

α-Adrenoceptor Subtypes

Initially classified as either α or β subtype receptors, based on anatomical location and functional considerations, more recent pharmacological and molecular biological techniques have identified the heterogeneity of the receptors and led to the identification of numerous subtypes of each receptor. α-adrenoceptors exist on peripheral sympathetic nerve terminals and are divided into two subtypes, $\alpha_1$ and $\alpha_2$. $\alpha_1$ is found mostly postsynaptically, while $\alpha_2$, although typically sited presynaptically, can also occur postsynaptically. These initial subtypes were further divided into $\alpha_{1A}$, $\alpha_{1B}$ and $\alpha_{1D}$ receptors (by pharmacological methods), each with distinct sequences and tissue distributions, and $\alpha_{1a}$, $\alpha_{1b}$, and $\alpha_{1d}$ by molecular biological and cloning techniques (note lower case letters refer to cloned receptors). Similarly, work done to identify subtypes of the $\alpha_2$ adrenoeceptor has led to the discovery of a subclasses $\alpha_{2A}$, $\alpha_{2B}$, $\alpha_{2C}$, $\alpha_{2D}$, and $\alpha_{2C10}$.

$\alpha_1$-Adrenoceptor Location and Function $\alpha_1$-adrenoceptors are found both in the central and peripheral nervous system. In the Central Nervous System they are found mostly postsynaptically and have an excitatory function. Peripherally, they are responsible for contraction and are situated on vascular and non-vascular smooth muscle. $\alpha_1$-adrenoceptors on vascular smooth muscle are located intrasynaptically and function in response to neurotransmitter release. For non-vascular smooth muscle, they can be found on the liver, where they cause hepatic glycogenolysis and potassium release. On heart muscle they mediate a stimulatory (positive inotropic) effect. In the gastrointestinal system they cause relaxation of gastrointestinal smooth muscle and decrease salivary secretion.

Transduction Mechanisms

All $\alpha$-adrenoceptors use G-proteins as their transduction mechanism. Differences occur in the type of G-protein the receptors are coupled to $\alpha_1$-adrenoceptors are coupled through the Gp/Gq mechanism, whereas $\alpha_2$-adrenoceptors are coupled through different G-proteins. Gp/Gq activates phospholipase C that phosphorolates phosphatidyl inositol to produce inositol triphosphate and diacylglycerol. These compounds act as second messengers and cause release of calcium from intracellular stores in the sarcoplasmic reticulum, and activation of calcium channels respectively. They thus produce their effects by the release of calcium from intracellular stores.

Clinical Uses

The clinical uses of adrenergic compounds are vast. The treatment of many medical conditions can be attributed to the action of drugs acting on adrenergic receptors. For example, $\alpha$-adrenoceptor ligands can be used in the treatment of hypertension. Drugs such as prazosin, an $\alpha_1$-adrenoceptor antagonist and clonidine, an $\alpha_2$-adrenoceptor agonist both have antihypertensive effects. $\alpha_1$-adrenoceptor antagonists are also employed in the treatment of benign prostatic hypertrophy.

Several sympathomimetic drugs are used primarily as vasoconstrictors for local application to nasal and ocular mucous membranes (see Table 1). $\alpha$-adrenoceptor agonists are used extensively as nasal decongestants in patients with allergic or vasomotor rhinitis and in acute rhinitis in patients with upper respiratory infections (EMPEY and MEDDER, 1981). These drugs probably decrease the resistance to airflow by decreasing the volume of the nasal mucosa. The receptors that mediate this effect appear to be the $\alpha_1$-adrenoceptors, though $\alpha_2$-adrenoceptors may be responsible for contraction of arterioles that supply the nasal mucosa. While a major limitation of therapy with nasal decongestants is that of a loss of efficacy with prolonged use, agonists that are selective for $\alpha_1$ receptors may be less likely to induce mucosal damage (DEBERNARDIS et al 1987). As an ocular decongestant, to decrease swelling and redness of the eyes, $\alpha$-adrenoceptor agonists are widely used in the treatment of allergic conjunctivitis, whether seasonal ('hay fever') or perennial.

The use of a topically applied $\alpha_1$-adrenoceptor agonist preparation to the skin, however, is hitherto unknown to this art and would be desirable to provide a method of treating skin affected by rosacea or other conditions of increased cutaneous erythema.

TABLE 1

Characterisation of $\alpha$-adrenoceptors:

| Receptor Type | $\alpha_1$ | $\alpha_2$ |
|---|---|---|
| Selective Agonist | Phenylephrine Oxymetazoline | Clonidine Clenbuterol |
| Selective Antagonist | Doxazosin Prazosin | Yohimbine Idazoxan |
| Agonist Potency Order | A = NA >> ISO | A = NA >> ISO |
| Second Messengers and Effectors | PLC activation via Gp/q causes inc. $[Ca^{2+}]_i$ | dec. cAMP via Gi/o causes dec. $[Ca^{2+}]_i$ |
| Physiological Effect | Smooth muscle contraction | Inhibition of transmitter release Hypotension, anaesthesia, Vasoconstriction |

Link to IUPHAR nomenclature: alpha-1 table or alpha-2 table

SUMMARY OF THE INVENTION $\alpha_1$-adrenoceptor agonist have been used to constrict blood vessels or minimize redness on ocular mucosal tissue to treat conjunctival redness, to nasal mucosa, as a decongestant for the treatment of allergic rhinitis, and for rectal mucosal administration suitable for curing hemorrhoids. However, to date it was not envisaged to use $\alpha_1$-adrenoceptor agonists for treating skin redness. It has now been observed that $\alpha_1$-adrenoceptor agonists are useful for eliciting a preventive and/or therapeutic effect on decreasing skin redness when applied topically to the skin.

Accordingly, it is an object of the present invention to provide a novel method for treating rosacea and other conditions of the skin characterized by increased erythema (redness).

Another object of the present invention to provide novel topical compositions for treating rosacea and other conditions of the skin characterized by increased erythema (redness).

It is another and more specific object of the present invention to provide such compositions that include the formulation of at least one $\alpha_1$-adrenoceptor agonist into a cosmetic, pharmaceutical or dermatological composition for decreasing and/or preventing skin redness and irritation as exhibited in rosacea or other conditions of the skin characterized by increased erythema and to administer said compositions to a mammal, notably a human, in order to treat or prevent the disease states indicated above.

Additionally, it is an object of the present invention to provide such compositions that include the formulation of at least one $\alpha_1$-adrenoceptor agonist into a cosmetic, pharmaceutical or dermatological composition for decreasing and/or preventing skin redness and irritation as exhibited in rosacea or other conditions of the skin characterized by increased erythema in combination and admixed with other agents known to be effective in treating other manifestations of said skin conditions and to administer said compositions to a mammal, notably a human, in order to treat or prevent the manifestations of the disease states indicated above.

The present invention is achieved by the provision of methods of treating rosacea or other conditions of the skin characterized by increased erythema, in a patient in need of such treatment, comprising the topical administration of a therapeutically effective amount of a composition comprising at least one $\alpha_1$-adrenoceptor agonist. $\alpha_1$-adrenoceptor agonists include, but are not limited to, oxymetazoline hydrochloride, tetrahydrozoline hydrochloride, naphazoline hydrochloride and phenylepherine hydrochloride. Preferably, the composition comprises at least one $\alpha_1$-adrenoceptor agonist formulated in a pharmaceutically/dermatologically acceptable medium, preferably a gel, cream, lotion or solution which is preferably administered by spreading the gel, cream, lotion or solution onto the affected area.

Preferred embodiments may also include enhancers of cutaneous penetration or inhibitors or regulators of cutaneous penetration as required to increase therapeutic efficacy and/or decrease systemic absorption and any potential undesirable systemic effects of the active agent(s).

DETAILED DESCRIPTION OF THE PREFERRED EMBODIMENT

The present invention is based at least in part on the clinical observation that the topical application of a therapeutically effective amount of a composition comprising at least one $\alpha_1$-adrenoceptor agonist to the skin is effective in significantly reducing or preventing the redness (erythema), flushing and sensation of warmth and discomfort which are hallmarks of rosacea and other conditions causing discreet erythema of the skin (e.g. acne, sunburn), and thus provides both subjective and objective relief of signs and symptoms of these conditions. Prototypical $\alpha_1$-adrenoceptor agonists include phenylepherine and oxymetazoline, but other al-adrenoceptor agonist agents include, but are not limited to naturally occurring and synthetically derived compounds based on or derived from pharmacologically similarly acting chemicals, drugs or prodrugs and derivatives thereof. Examples of preferred compounds which are specifically contemplated as $\alpha_1$-adrenoceptor agonists suitable for use in accordance with the present invention include, but are not limit to e.g., the $\alpha_1$-adrenoceptor agonists oxymetazoline, tetrahydrozoline, nephazoline, xylometazoline and the $\alpha_1$-adrenoceptor agonists discussed in chapters 6 and 10 of Goodman and Gilman's The Pharmacological Basis of Therapeutics, Tenth Edition, edited by Hardman J and Limbird L. New York, N.Y., McGraw-Hill, 2001, which is hereby incorporated by reference as though set forth in full herein, and in particular oxymetazoline hydrochloride, tetrahydrozoline hydrochloride, naphazoline hydrochloride, xylometazoline hydrochloride, phenylephrine, phenylephrine hydrochloride, methoxamine, methoxamine hydrochloride, mephentermine, mephentermine sulfate, metaraminol, metaraminol bitartrate, desglymidodrine, and its prodrug midodrine.

As no prior consideration of the application of $\alpha_1$-adrenoceptor agonist to the skin has been contemplated or reported, for any indication, little is known of the cutaneous absorption or toxicology of oxymetazoline used in this fashion. The manufacturers report no significant organ damage or general toxicity in dog, cat, rabbit or mouse about dosages close to those used in man. When administered by injection subcutaneously, in rabbits, no drug related abnormalities or effects on the offspring were found. In a retrospective study in man, no association was found between the drug and congenital disorders. No carcinogenicity tests have been reported. But oxymetazoline has been used intranasaly and ophthalmicaly for decades for reducing blood flow and diminishing of swelling of the mucosa and has not been reported to effect any systemic side effects. There is no formal data on the subject, however. The excellent safety and efficacy profile of oxymetazoline when used intranasaly or ophthalmicaly to effect local vasoconstriction suggested its potential use as a topically applied vasoconstrictor to the skin for the treatment of the erythema and telangiectasias of rosacea and other erythematous conditions of the skin and has been observed clinically by one of the applicants in his clinical practice of dermatology. The local anti-erythema effect is thus observed when topically applying an effective amount of an $\alpha_1$-adrenoceptor agonist, admixed with a skin-specific penetration enhancer and a pharmacologically acceptable vehicle for topical administration without causing any noticeable systemic effects. The clinical efficacy of the applied $\alpha_1$-adrenoceptor agonist compound is predicated not only upon the agent reaching the receptors, which are located within the skin on vascular smooth muscle, but also on the pharmacokinetics of each particular receptor agonist. Thus the choice and concentration of the active agent, or combination of active agents, the topical delivery system and vehicle for the active agent(s) are significant considerations.

Specifically, prototypical $\alpha_1$-adrenoceptor agonists in the present invention are tetrahydrozoline and oxymetazoline, and when included in the typical embodiment as the sole active ingredient (sole $\alpha_1$-adrenoceptor agonist) are preferably used in amounts of about 0.05% up to about 30%, and preferably about 0.001% up to about 3% by weight based on the total weight of the composition. Where both, or an additional or different $\alpha_1$-adrenoceptor agonist is admixed, lower amounts of the active compound(s) might be included. Additionally, the carrier or vehicle of the invention will have dramatic effects on the concentrations of the active ingredients selected. The preferred embodiments employ active ingredients in amounts effective to achieve clinical efficacy without causing systemic side effects.

The compositions according to the invention may comprise all pharmaceutical forms normally utilized for the topical route of administration and known to practitioners of this art including solutions, gels, lotions creams, ointments, foams, mousses, emulsions, microemulsions, milks, serums, aerosols, sprays, dispersions, microcapsules, vesicles and microparticles thereof. The subject compositions may also be formulated as solid preparations constituting soaps or cleansing bars. These compositions are formulated according to conventional techniques.

The term "pharmacologically/dermatologically acceptable carriers", as used herein, means that the carrier is suitable for topical application to the keratinous tissue, has good aesthetic properties, is compatible with the active agents of the present invention and any other components, and will not cause any untoward safety or toxicity concerns.

The carrier can be in a wide variety of forms. For example, emulsion carriers, including, but not limited to, oil-in-water, water-in-oil, water-in-oil-in-water, and oil-in-water-in-silicon emulsions, are useful herein. As will be understood by the skilled artisan, a given component will distribute primarily into either the water or oil/silicon phase, depending on the water solubility/dispersibility of the component in the composition. A safe and effective amount of carrier is from about 50% to about 99.999%, more preferably from about 70% to about 99.99%.

The composition, if desired, can contain various known bases such as excipients, binders, lubricants, and disintegrants. If desired, it can also contain oily materials such as various fats, oils, waxes, hydrocarbons, fatty acids, higher alcohols, ester oils, metallic soaps, animal or vegetable extracts, hydrophilic or lipophilic gelling agents, hydrophilic or lipophilic active agents, pharmaceutically effective components such as vitamins, hormones, amino acids, surfactants, colorants, dyes, pigments, fragrances, odor absorbers, antiseptics, preservatives, bactericides, humectants, thickeners, solvents, fillers, antioxidants, sequestering agents, sunscreens, or any other known components and additives as long as the effects of the present invention are not impaired.

Examples of suitable oils includes mineral oils, plant oils such as peanut oil, sesame oil, soybean oil, safflower oil, sunflower oil, animal oils such as lanolin or perhydrosqualene, synthetic oils such as purcellin oil, silicone oils such as cyclomethicome among others. Fatty alcohols, fatty acids such as stearic acid and waxes such as paraffin wax, carnauba wax or beeswax may also be used as fats.

The composition may also contain emulsifying agents such as glyceryl stearate, solvents such as lower alcohols including ethanol, isopropanol, and propylene glycol, hydrophilic gelling agents including carboxyvinyl polymers or acrylic copolymers, polyacrylamides, polysaccharides, lipophilic gelling agents or fatty acid metal salts among others, hydrophilic acting agents such as amino acids, sugars, starch or urea, lipophilic active agents such as retinol or tocopherol.

In some embodiments, the compositions contain one or more $\alpha_1$-adrenoceptor agonists, to act specifically on the erythematous component of the condition to be treated, admixed with another agent known to be effective in treating another manifestation of the disease state. For example, compositions consisting of anti-rosacea agents such as metronidazole, precipitated sulfur, sodium sulfacetamide, or azelaic acid, which are commonly used to treat the papular and pustular components of rosacea are combined with a dermatologically/pharmacologically acceptable form of the subject $\alpha_1$-adrenoceptor agonist to effect treatment of both the inflammatory (papular and pustular) and erythematous manifestations of the condition. There is currently no known composition available that succeeds in this goal.

Other embodiments combine one or more $\alpha_1$-adrenoceptor agonist with active agents destined, in particular, for preventing and/or treating the erythema associated with numerous other skin complaints, conditions and afflictions. Examples of these agents include:

1. Antirosacea agents such as metronidazole, precipitated sulfur, sodium sulfacetamide, or azelaic acid.
2. Antibacterial agents (antibiotics) such as clindamycin phosphate, erythromycin, or antibiotics from the tetracycline family.
3. Antimycobacterial agents such as dapsone.
4. Other antiacne agents such as retinoids, or benzoyl peroxide.
5. Antiparasitic agents such as metronidazole, permethrin, crotamiton or pyrethroids.
6. Antifungal agents such as compounds of the imidazole family such as miconazole, clotrimazole, econazole, ketoconazole, or salts thereof, polyene compounds such as amphotericin B, compound of the allylamine family such as terbinafine.
7. Steroidal anti-inflammatory agents such as hydrocortisone triamcinolone, fluocinonide, betamethasone valerate or clobetasol propionate, or non-steroidal anti-inflammatory agents such as ibuprofen and salts thereof, naproxen and salts thereof, or acetaminophen.
8. Anesthetic agents such as lidocaine, prilocalne, tetracaine, Hydrochloride and derivatives thereof.
9. Antipruriginous agents such as thenaldine, trimeprazine, or pramoxine.
10. Antiviral agents such as acyclovir.
11. Keratolytic agents such as alpha- and beta-hydroxy acids such as glycolic acid or salicylic acid, or urea.
12. Anti-free radical agents (antioxidants) such as Vitamin E (alpha tocopherol) and its derivatives, Vitamin C (ascorbic acid), Vitamin A (retinol) and its derivatives, and superoxide dismutases.
13. Antiseborrheic agents such as zinc pyrithione and selenium sulfide.
14. Antihistamines such as cyproheptadine or hydroxyzine.
15. Tricyclic antidepressants such as doxepin hydrochloride.

In order to further illustrate the present invention and the advantages thereof, the following specific examples are given, it being understood that the same are illustrative and in no ways limitative.

The administration of compositions containing one or more alpha-1 adrenoreceptor agonists elicits a marked decrease or even complete disappearance of skin redness, which is manifested both in rosacea and other discreet erythemas.

Specifically, according to the present invention, at least one alpha-1 adrenoreceptor agonist is formulated into a cosmetic, pharmaceutical or dermatological composition for treating skin redness of vascular origin, evident in rosacea and/or other discreet erythemas including acne and sunburn.

The compositions of the invention will be, preferably, administered topically. The subjective compositions for topical application comprise a cosmetically, pharmaceutically or dermatologically acceptable medium (vehicle, diluent or carrier), namely a medium which is compatible with application to the skin.

The present invention is directed to the use of alpha 1 and 2 adrenoreceptor agonists for treat rosacea or erythema. In one embodiment, the invention is directed to the use alpha 1 agonists such oxymetazoline hydrochloride as a vasoconstrictor for use with or without an anti-acne compound. Alternative alpha 1 agonists including Phenylephrine are applicable to the teachings of the present invention. The principles of the present invention are also deemed to be applicable to alpha 2 adrenoreceptor agonists such as Clonidine and Clenbuterol.

For the purposes of this disclosure, rosacea is characterized by erythema of the face, predominantly on the cheeks, the forehead and the nose, hyperseborrhoea of the face on the forehead, the nose and the cheeks, and an infectious component manifesting acne form pustules. Moreover, these indications are associated with a neurogenic component, namely, a cutaneous hyperreactivity of the skin of the face and of the neck, characterized by the appearance of redness and subjective sensations of the itching or pruritus type, sensations of burning or of heating, sensations of stinging, tingling, discomfort, tightness, etc.

The preferred alpha 1 or 2 agonist used as a vasoconstrictor in the present invention is preferably used in an amount of about 0.01% up to about 20%, and preferably about 0.1% to about 10%, by weight based on the total weight of the composition. In the most preferred embodiment, the vasoconstrictor comprises an alpha 1 or alpha 2 adrenoreceptor agonist. The vasoconstrictor used in the present invention may function to remove the redness from acne areas of the skin, including oxymetazoline hydrochloride, the preferred agonist in the present invention oxymetazoline hydrochloride: The chemical formula for oxymetazoline hydrochloride is as follows:
2-(3-Hydroxy-2,6-dimethyl-4-t-butylbenzyl)-2-imidazoline hydrochloride Oxymetazoline Hydrochloride: Structural Formula:

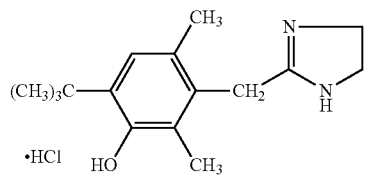

The following table sets forth the characteristics of alpha 1 and alpha 2 adrenoreceptors as used in the present invention.

| Receptor Type | $\alpha_1$ | $\alpha_2$ |
| --- | --- | --- |
| Selective Agonist | Phenylephrine Oxymetazoline | Clonidine Clenbuterol |
| Selective Antagonist | Doxazosin Prazosin | Yohimbine Idazoxan |
| Agonist Potency Order | A = NA >> ISO | A = NA >> ISO |
| Second Messengers and Effectors | PLC activation via Gp/q causes inc. $[Ca^{2+}]_i$ | dec. cAMP via Gi/o causes dec. $[Ca^{2+}]_i$ |
| Physiological Effect | Smooth muscle contraction | Inhibition of transmitter release Hypotension, anaesthesia, Vasoconstriction |

The present invention has been described with reference to the enclosed preferred embodiment. The true nature and scope of the present invention is to be determined with reference to the claims appended hereto.

The invention claimed is:

1. A method of treating erythema resulting from rosacea in a subject comprising administering topically to the skin of said subject in need thereof a composition comprising a therapeutically effective amount of an $\alpha_1$-adrenoreceptor agonist as the sole active agent for decreasing said erythema resulting from rosacea, wherein said $\alpha_1$-adrenoreceptor agonist is selected from tetrahydrozoline, tetrahydrozoline hydrochloride, naphazoline, naphazoline hydrochloride, xylometazoline, xylometazoline hydrochloride, oxymetazoline and oxymetazoline hydrochloride.

2. The method of claim 1, wherein said composition is selected from solutions, gels, lotions, creams, ointments, foams, mousses, emulsions, microemulsions, milks, serums, aerosols, sprays, dispersions, microcapsules, vesicles and microparticles thereof.

3. The method of claim 1, wherein said composition is selected from soaps and cleansing bars.

4. The method of claim 1, wherein said composition is a cream.

5. The method of claim 1, wherein said composition is a gel.

6. The method of claim 1, wherein said composition is a lotion.

7. The method of claim 1, wherein said erythema resulting from rosacea is elicited by at least one factor selected from the group consisting of intake of food, of hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics.

8. The method of claim 1, wherein said composition comprises about 0.1% to about 10% of said $\alpha_1$-adrenoreceptor agonist.

9. The method of claim 1, wherein said composition further comprises about 50% to about 99.999% of a carrier.

10. The method of claim 1, wherein said composition further comprises about 70% to about 99.99% of a carrier.

11. The method of claim 1, wherein said composition comprises about 0.05% to about 30% of said $\alpha_1$-adrenoreceptor agonist.

12. The method of claim 1, wherein said composition comprises about 0.01% to about 20% of said $\alpha_1$-adrenoreceptor agonist.

13. The method of claim 1, wherein said composition comprises about 0.001% to about 3% of said $\alpha_1$-adrenoreceptor agonist.

* * * * *